United States Patent [19]

Cotrel et al.

[11] 4,021,554

[45] May 3, 1977

[54] 1,4-OXATHIINO[2,3-c]PYRROLE DERIVATIVES

[75] Inventors: Claude Cotrel, Paris; Claude Jeanmart, Brunoy; Michel Barreau, Paris, all of France

[73] Assignee: Rhone-Poulenc Industries, Paris, France

[22] Filed: Nov. 5, 1975

[21] Appl. No.: 628,927

[30] Foreign Application Priority Data

Nov. 7, 1974 France .......................... 74.36962

[52] U.S. Cl. .......................... 424/250; 260/268 BC
[51] Int. Cl.² ...................................... C07D 411/14
[58] Field of Search ............... 260/250 A, 268 BC; 424/250

[56] References Cited

OTHER PUBLICATIONS

Ten Haken P. Chemical Abstracts vol. 74, 22741x, (1971).

*Primary Examiner*—Donald G. Daus
*Assistant Examiner*—Jose Tovar
*Attorney, Agent, or Firm*—Stevens, Davis, Miller & Mosher

[57] ABSTRACT 1,4-Oxathiino[2,3-c]pyrrole derivatives of the formula:-

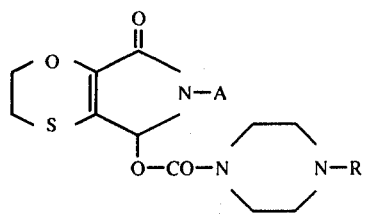

wherein A represents a phenyl, 2-pyridyl, 3-pyridazinyl, 2-quinolyl or naphthyridinyl radical, or a said radical substituted by one or two atoms or radicals selected from halogen, alkyl of 1 through 4 carbon atoms, alkoxy of 1 through 4 carbon atoms and nitro, and R represents alkyl of 1 through 4 carbon atoms, cycloalkyl of 3 through 6 carbon atoms, alkenyl of 2 through 4 carbon atoms or alkynyl of 2 through 4 carbon atoms, possess pharmacological properties, and are especially useful as tranquillizers, anti-convulsant agents, decontracturants, and agents to produce hypnosis.

9 Claims, No Drawings

1,4-OXATHIINO[2,3-c]PYRROLE DERIVATIVES

This invention relates to new therapeutically useful 1,4-oxathiino[2,3-c]pyrrole derivatives, processes for their preparation and pharmaceutical compositions containing them.

The new 1,4-oxathiino[2,3-c]pyrrole derivatives of the present invention are those of general formula:

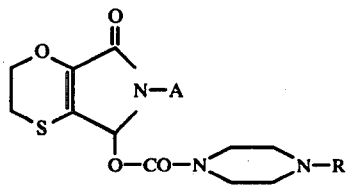

wherein A represents a phenyl, 2-pyridyl, 3-pyridazinyl, 2-quinolyl or naphthyridinyl radical, each such radical being optionally substituted by one or two atoms or radicals, which — when two substituents are present — may be the same or different, selected from halogen atoms (preferably chlorine), alkyl radicals containing from 1 to 4 carbon atoms (preferably methyl), alkoxy radicals containing from 1 to 4 carbon atoms (preferably methoxy), and the nitro radical, and R represents an alkyl radical containing from 1 to 4 carbon atoms (preferably methyl), a cycloalkyl radical containing from 3 to 6 carbon atoms (for example cyclohexyl), an alkenyl radical containing 2 to 4 carbon atoms (preferably allyl) or an alkynyl radical containing 2 to 4 carbon atoms (for example propargyl), and acid addition salts thereof.

According to a feature of the present invention, the compounds of general formula I are prepared by the process which comprises reacting a 1-chlorocarbonyl-piperazine of the general formula:

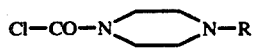

(wherein R is as hereinbefore defined) with a 1,4-oxathiino[2,3-c]pyrrole derivative of the general formula:

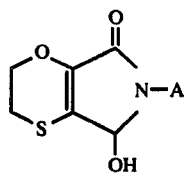

wherein A is as hereinbefore defined.

The reaction can be carried out either by reacting a piperazine derivative of general formula II with an alkali metal salt, optionally prepared in situ, of a compound of general formula III in an anhydrous organic solvent, for example tetrahydrofuran or dimethylformamide, at a temperature at or below about 60° C., or by reacting an acid addition salt of the piperazine derivative of general formula II, preferably the hydrochloride, with a compound of general formula III in the presence of a condensing agent such as pyridine and optionally in the presence of a strong organic base such as a tertiary amine, more particularly triethylamine, at a temperature between about 20° C. and the reflux temperature of the reaction mixture.

The 1,4-oxathiino[2,3-c]pyrrole derivatives of general formula III can be prepared by partial reduction of an imide of the general formula:

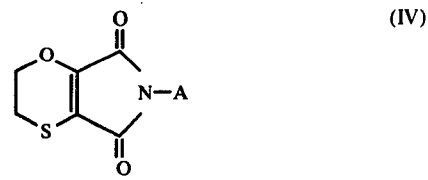

wherein A is as hereinbefore defined. The reduction is generally effected by means of an alkali metal borohydride in an organic solvent, for example methanol.

The imides of general formula IV can be obtained by reacting an amine of the general formula $H_2N-A$ (wherein A is as hereinbefore defined) with 5,6-dihydro-1,4-oxathiine-2,3-dicarboxylic acid anhydride. The reaction is generally carried out by heating the reactants at a temperature between 160° and 240° C. in an organic solvent, for example ethanol, diphenyl ether, acetic acid, dimethylformamide or acetonitrile, and optionally in the presence of a condensing agent such as dicyclohexylcarbodiimide, or at a temperature between 50° and 80° C. in an organic solvent, for example dimethylformamide, in the presence of hydroxysuccinimide and dicyclohexylcarbodiimide.

5,6-Dihydro-1,4-oxathiine-2,3-dicarboxylic acid anhydride can be prepared by the method described by P. ten Haken, J. Het. Chem., 7, 1211 (1970).

According to another feature of the invention, the compounds of general formula I are prepared by the process which comprises reacting a piperazine derivative of the general formula:

(wherein R is as hereinbefore defined) with a mixed carbonate of the general formula:

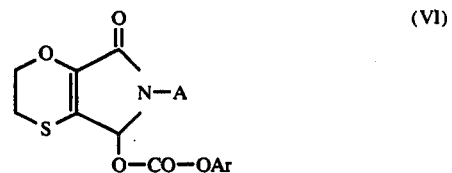

wherein A is as hereinbefore defined and Ar represents a phenyl radical optionally substituted by an alkyl radical containing 1 to 4 carbon atoms or a nitro radical. The reaction is generally carried out in an organic solvent, for example acetonitrile or dimethylformamide, at a temperature between 0° and 50° C.

The mixed carbonates of general formula VI can be obtained by reacting a chloroformate of the general formula:

(wherein Ar is as hereinbefore defined) with a 1,4-oxathiino[2,3-c]pyrrole derivative of general formula III.

The 1,4-oxathiino[2,3-c]pyrrole derivatives of general formula I obtained by the aforementioned processes can be purified by physical methods such as distillation, crystallisation or chromatography, or by chemical methods such as the formation of salts, crystallisation of the salts and decomposition of them in an alkaline medium. In carrying out the said chemical methods the nature of the anion of the salt is immaterial, the only requirement being that the salt must be well-defined and readily crystallisable.

The 1,4-oxathiino[2,3-c]pyrrole derivatives of general formula I may be converted by methods known per se into acid addition salts. The acid addition salts may be obtained by the action of acids on the new compounds in appropriate solvents. As organic solvents there may be used alcohols, ethers, ketones or chlorinated hydrocarbons. The salt which is formed is precipitated, if necessary after concentration of the solution, and is isolated by filtration or decantation.

By the term "methods known per se" as used in this specification is meant methods heretofore used or described in the chemical literature.

The 1,4-oxathiino[2,3-c]pyrrole derivatives of the invention and their acid addition salts possess valuable pharmacological properties; they are particularly active as tranquillisers, anti-convulsant agents, decontracturants and agents to produce hypnosis. In animals (mice), they have proved active as such at doses of between 0.1 and 100 mg./kg. animal body weight when administered orally, in particular in the following tests:

i. electric battle according to a technique similar to that of Tedeschi et al [J. Pharmacol., 125, 28 (1959)],
ii. pentetrazole-induced convulsion according to a technique similar to that of Everett and Richards [J. Pharmacol., 81, (1944)].
iii. supramaximal electric shock according to the technique of Swinyard et al [J. Pharmacol., 106, 319 (1952)], and
iv. mortality due to strychnine according to a technique similar to that of F. Barzaghi et al, Arzneimittel Forschung, 23, 683 (1973).

The $LD_{50}$ of the compounds of the invention when administered orally to mice is generally about, or greater than, 900 mg./kg. animal body weight.

For therapeutic purposes, the 1,4-oxathiino[2,3-c]pyrrole derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-$\beta$-hydroxynaphthoates) so that the beneficial physiological properties inherent in the bases are not vitiated by side effects ascribable to the anions.

Compounds of general formula I of particular interest are those in which A represents a phenyl, 2-pyridyl, 3-pyridazinyl, 2-quinolyl or 1,8-naphthyridin-2-yl radical, optionally substituted by a halogen atom or a methyl, methoxy or nitro radical, and R represents a methyl radical or an alkenyl radical containing 2 to 4 carbon atoms. Of more outstanding interest are those compounds of general formula I in which A represents a 2-pyridyl, 2-quinolyl or 1,8-naphthyridin-2-yl radical substituted by a chlorine atom or a methyl or methoxy radical and R represents a methyl or allyl radical, and expecially 6-(7-methoxy-1,8-naphthyridin-2-yl)-5-(4-methylpiperazin-1-yl)carbonyloxy-7-oxo-2,3,6,7-tetrahydro-5H-1,4-oxathiino-[2,3-c]pyrrole, 6-(7-chloroquinol-2-yl)-5-(4-methylpiperazin-1-yl)carbonyloxy-7-oxo-2,3,6,7-tetrahydro-5H-1,4-oxathiino-[2,3-c]pyrrole, 6-(5-chloropyrid-2-yl)-5-(4-methylpiperazin-1-yl)carbonyloxy-7-oxo-2,3,6,7-tetrahydro-5H-1,4-oxathiino[2,3-c]pyrrole, 5-(4-methylpiperazin-1-yl)-carbonyloxy-6-(5-methylpyrid-2-yl)-7-oxo-2,3,6,7-tetrahydro-5H-1,4-oxathiino[2,3-c]pyrrole, 6-(7-chloro-1,8-naphthyridin-2-yl)-5-(4-methylpiperazin-1-yl)carbonyloxy-7-oxo-2,3,6,7-tetrahydro-5H-1,4-oxathiino[2,3-c]pyrrole, and 5-(4-allylpiperazin-1-yl)carbonyloxy-6-(7-chloro-1,8-naphthyridin-2-yl)-7-oxo-2,3,6,7-tetrahydro-5H-1,4-oxathiino[2,3-c]pyrrole.

The following Examples illustrate the invention.

EXAMPLE 1

Triethylamine (10.1 cc.) followed by pyridine (45 cc.) are added to a suspension of 6-(5-chloropyrid-2-yl)-5-hydroxy-7-oxo-2,3,6,7-tetrahydro-5H-1,4-oxathiino-[2,3-c]pyrrole (5.12 g.) and 1-chlorocarbonyl-4-methylpiperazine hydrochloride (10.7 g.) in methylene chloride (90 cc.). The reaction mixture is then heated to a temperature of about 50° C. for 2 hours 15 minutes. After cooling, the solution obtained is poured into a mixture of water (500 cc.) and methylene chloride (100 cc.). The aqueous layer is decanted and washed with methylene chloride (2 × 50 cc.). The organic layers are combined, washed by decanting with water (2 × 100 cc.), N aqueous sodium hydroxide solution (100 cc.) and water (2 × 100 cc.), dried over anhydrous sodium sulphate, filtered and evaporated to dryness under reduced pressure. After recrystallising the residue from acetonitrile (60 cc.), 6-(5-chloropyrid-2-yl)-5-(4-methylpiperazin-1-yl)carbonyloxy-7-oxo-2,3,6,7-tetrahydro-5H-1,4-oxathiino[2,3-c]pyrrole (4.6 g.), melting at 193° C., is obtained.

6-(5-Chloropyrid-2-yl)-5-hydroxy-7-oxo-2,3,6,7-tetrahydro-5H-1,4-oxathiino[2,3-c]pyrrole employed as starting material can be prepared by adding potassium borohydride (1.24 g.) to a suspension of 6-(5-chloropyrid-2-yl)-5,7-dioxo-2,3,6,7-tetrahydro-5H-1,4-oxathiino[2,3-c]-pyrrole (6.5 g.) in methanol (40 cc.). The temperature of the reaction mixture rises to about 35° C. After 10 minutes, the suspension obtained is cooled and then poured into water (300 cc.). The insoluble product is filtered off, and washed with water (3 × 30 cc.) and then with methanol (2 × 10 cc.). After drying, 6-(5-chloropyrid-2-yl)-5-hydroxy-7-oxo-2,3,6,7-tetrahydro-5H-1,4-oxathiino[2,3-c]pyrrole (5.5 g.), melting at 202° C., is obtained.

6-(5-Chloropyrid-2-yl)-5,7-dioxo-2,3,6,7-tetrahydro-5H-1,4-oxathiino[2,3-c]pyrrole can be prepared by heating a suspension of 5,6-dihydro-1,4-oxathiine-2,3-dicarboxylic acid anhydride (5.2 g.) and 2-amino-5-chloropyridine (3.88 g.) in diphenyl ether (25 cc.) and acetic acid (0.5 cc.) to a temperature of about 200° C. for 1 hour 10 minutes. After cooling to a temperature of about 70° C., diisopropyl ether (200 cc.) is added to the solution obtained. After cooling, the resulting solid residue is filtered off and washed with diisopropyl ether (3 × 20 cc.). After drying, 6-(5-chloropyrid-2-yl)-5,7-dioxo-2,3,6,7-tetrahydro-5H-1,4-oxathiino[2,3-c]-pyrrole (7 g.), melting at 152° C., is obtained.

2-Amino-5-chloropyridine can be prepared in accordance with the method described by F. Friedrich et al., Pharmazie, 19, (10), 677 (1964).

5,6-Dihydro-1,4-oxathiine-2,3-dicarboxylic acid anhydride can be prepared in accordance with the method described by P. ten Haken, J. Het. Chem., 7, 1211 (1970).

EXAMPLE 2

Following the procedure of Example 1 but starting with 5-hydroxy-6-(7-methoxy-1,8-naphthyridin-2-yl)-7-oxo-2,3,6,7-tetrahydro-5H-1,4-oxathiino[2,3-c]pyrrole (4.25 g.) and 1-chlorocarbonyl-4-methylpiperazine hydrochloride (10.5 g.) suspended in a mixture of triethylamine (7.8 g.), anhydrous pyridine (42.5 cc.) and methylene chloride (50 cc.), 6-(7-methoxy-1,8-naphthyridin-2-yl)-5-(4-methylpiperazin-1-yl)carbonyloxy-7-oxo-2,3,6,7-tetrahydro-5H-1,4-oxathiino[2,3-c]pyrrole (2.4 g.), melting at 258° C., is obtained after recrystallisation from acetonitrile.

5-Hydroxy-6-(7-methoxy-1,8-naphthyridin-2-yl)-7-oxo-2,3,6,7-tetrahydro-5H-1,4-oxathiino[2,3-c]pyrrole employed as starting material can be prepared by reaction of potassium borohydride (0.68 g.) with 6-(7-methoxy-1,8-naphthyridin-2-yl)-5,7-dioxo-2,3,6,7-tetrahydro-5H-1,4-oxathiino[2,3-c]pyrrole (4.23 g.) in methanol (45 cc.). 5-Hydroxy-6-(7-methoxy-1,8-naphthyridin-2-yl)-7-oxo-2,3,6,7-tetrahydro-5H-1,4-oxathiino[2,3-c]pyrrole (4.25 g.), melting at 222° C., is obtained.

6-(7-Methoxy-1,8-naphthyridin-2-yl)-5,7-dioxo-2,3,6,7-tetrahydro-5H-1,4-oxathiino[2,3-c]pyrrole can be prepared by reaction of 2-amino-7-methoxy-1,8-naphthyridine (2.3 g.) with 5,6-dihydro-1,4-oxathiine-2,3-dicarboxylic acid anhydride (2.26 g.) in diphenyl ether (25 cc.) at a temperature of about 170° C. 6-(7-Methoxy-1,8-naphthyridin-2-yl)-5,7-dioxo-2,3,6,7-tetrahydro-5H-1,4-oxathiino[2,3-c]-pyrrole (2.73 g.), melting at 255° C., is obtained.

2-Amino-7-methoxy-1,8-naphthyridine may be prepared by reaction of sodium methoxide (21 g.) with 2-amino-7-chloro-1,8-naphthyridine (15 g.) in methanol (450 cc.) under reflux. This gives 2-amino-7-methoxy-1,8-naphthyridine (12.34 g.) melting at 154° C.

EXAMPLE 3

Following the procedure of Example 1 but starting with 6-(7-chloroquinol-2-yl)-5-hydroxy-7-oxo-2,3,6,7-tetrahydro-5H-1,4-oxathiino[2,3-c]pyrrole (4.47 g.) and 1-chlorocarbonyl-4-methylpiperazine hydrochloride (11 g.) suspended in a mixture of triethylamine (8.1 g.), anhydrous pyridine (45 cc.) and methylene chloride (55 cc.), 6-(7-chloroquinol-2-yl)-5-(4-methylpiperazin-1-yl)-carbonyloxy-7-oxo-2,3,6,7-tetrahydro-5H-1,4-oxathiino-[2,3-c]pyrrole (1.3 g.), melting at 228° C., is obtained after recrystallisation from acetonitrile.

6-(7-Chloroquinol-2-yl)-5-hydroxy-7-oxo-2,3,6,7-tetrahydro-5H-1,4-oxathiino[2,3-c]pyrrole employed as starting material can be prepared by reaction of potassium borohydride (0.72 g.) with 6-(7-chloroquinol-2-yl)-5,7-dioxo-2,3,6,7-tetrahydro-5H-1,4-oxathiino[2,3-c]pyrrole (4.6 g.) in methanol (50 cc.). 6-(7-Chloroquinol-2-yl)-5-hydroxy-7-oxo-2,3,6,7-tetrahydro-5H-1,4-oxathiino[2,3-c]pyrrole (4.47 g.), melting at 270° C., is thus obtained.

6-(7-Chloroquinol-2-yl)-5,7-dioxo-2,3,6,7-tetrahydro-5H-1,4-oxathiino[2,3-c]pyrrole can be prepared by reaction of 2-amino-7-chloroquinoline (3.78 g.) with 5,6-dihydro-1,4-oxathiine-2,3-dicarboxylic acid anhydride (3.44 g.) in diphenyl ether (40 cc.) at a temperature of about 180° C. This gives 6-(7-chloroquinol-2-yl)-5,7-dioxo-2,3,6,7-tetrahydro-5H-1,4-oxathiino[2,3-c]pyrrole (4.6 g.) melting at 218° C.

2-Amino-7-chloroquinoline can be prepared by heating a mixture of 2,7-dichloroquinoline (36.7 g.) and 16N ammonia (700 cc.) in an autoclave at 125° C. for 25 hours. After cooling, an insoluble product is isolated by filtration and then washed with water (120 cc.). After drying, a product (34 g.) melting at about 115°–120° C. is obtained. Recrystallisation from benzene (150 cc.) gives 2-amino-7-chloroquinoline (10 g.) melting at 175° C.

2,7-Dichloroquinoline can be prepared in accordance with the method described by R. E. Lutz et al., J. Amer. Chem. Soc., 68, 1322 (1946).

EXAMPLE 4

Triethylamine (6.2 cc.) followed by anhydrous pyridine (27.5 cc.) is added to a suspension of 5-hydroxy-6-(5-methylpyrid-2-yl)-7-oxo-2,3,6,7-tetrahydro-5H-1,4-oxathiino[2,3-c]pyrrole (2.9 g.) and 1-chlorocarbonyl-4-methylpiperazine hydrochloride (6.6 g.) in methylene chloride (55 cc.). The reaction mixture is then heated under reflux for 6 hours. After cooling, water (150 cc.) and methylene chloride (50 cc.) are added. The aqueous phase is decanted and washed with methylene chloride (50 cc.). The organic phases are combined and washed by decanting successively with water (2 × 50 cc.), N aqueous sodium hydroxide solution (50 cc.) and water (2 × 50 cc.). After drying over sodium sulphate and treatment with decolourising charcoal, the organic phase is evaporated to dryness under reduced pressure. Recrystallisation of the residue from acetonitrile (40 cc.) gives 5-(4-methylpiperazin-1-yl)carbonyloxy-6-(5-methylpyrid-2-yl)-7-oxo-2,3,6,7-tetrahydro-5H-1,4-oxathiino[2,3-c]pyrrole (2.8 g.) melting at 183° C.

5-Hydroxy-6-(5-methylpyrid-2-yl)-7-oxo-2,3,6,7-tetrahydro-5H-1,4-oxathiino[2,3-c]pyrrole employed as starting material can be prepared by reaction of potassium borohydride (0.94 g.) with 6-(5-methylpyrid-2-yl)-5,7-dioxo-2,3,6,7-tetrahydro-5H-1,4-oxathiino[2,3-c]pyrrole (4.6 g.) in methanol (35 cc.) at a temperature of about 30° C. This gives 5-hydroxy-6-(5-methylpyrid-2-yl)-7-oxo-2,3,6,7-tetrahydro-5H-1,4-oxathiino[2,3-c]pyrrole (3.1 g.) melting at 183° C.

6-(5-Methylpyrid-2-yl)-5,7-dioxo-2,3,6,7-tetrahydro-5H-1,4-oxathiino[2,3-c]pyrrole can be prepared by reaction of 2-amino-5-methylpyridine (2.16 g.) with 5,6-dihydro-1,4-oxathiine-2,3-dicarboxylic acid anhydride (3.44 g.) in diphenyl ether (1 cc.) at a temperature of about 200° C. This gives 6-(5-methylpyrid-2-yl)-5,7-dioxo-2,3,6,7-tetrahydro-5H-1,4-oxathiino[2,3-c]pyrrole (2.5 g.) melting at 155° C.

EXAMPLE 5

Following the procedure of Example 4 but starting with 6-(7-chloro-1,8-naphthyridin-2-yl)-5-hydroxy-7-oxo-2,3,6,7-tetrahydro-5H-1,4-oxathiino[2,3-c]pyrrole (3 g.) and 1-chlorocarbonyl-4-methylpiperazine hydrochloride (5.33 g.) in methylene chloride (45 cc.) in the presence of triethylamine (5 cc.) and pyridine (22 cc.), 6-(7-chloro-1,8-naphthyridin-2-yl)-5-(4-methylpiperazin-1-yl)-carbonyloxy-7-oxo-2,3,6,7-tetrahydro-5H-1,4-oxathiino[2,3-c]pyrrole (2.1 g.), melting at 308° C. with decomposition, is obtained.

6-(7-Chloro-1,8-naphthyridin-2-yl)-5-hydroxy-7-oxo-2,3,6,7-tetrahydro-5H-1,4-oxathiino[2,3-c]pyrrole employed as starting material can be prepared by reaction of potassium borohydride (0.54 g.) with 6-(7-chloro-1,8-naphthyridin-2-yl)-5,7-dioxo-2,3,6,7-tetrahydro-5H-1,4-oxathiino[2,3-c]pyrrole (3.59 g.) in methanol (30 cc.) at a temperature of about 30° C. This gives 6-(7-chloro-1,8-naphthyridin-2-yl)-5-hydroxy-7-oxo-2,3,6,7-tetrahydro-5H-1,4-oxathiino[2,3-c]pyrrole (3.06 g.) melting at 277° C.

6-(7-Chloro-1,8-naphthyridin-2-yl)-5,7-dioxo-2,3,6,7-tetrahydro-5H-1,4-oxathiino[2,3-c]pyrrole can be prepared by heating a solution of 5,6-dihydro-1,4-oxathiine-2,3-dicarboxylic acid anhydride (3.44 g.) with N-hydroxysuccinimide (2.86 g.) in anhydrous dimethylformamide (100 cc.) at a temperature of about 60° C. After heating for 18 hours, 2-amino-7-chloro-1,8-naphthyridine (3.6 g.) and dicyclohexylcarbodiimide (8 g.) are added to the reaction mixture. The reaction mixture is then heated at a temperature of about 75° C. for 24 hours. After cooling, water (1 cc.) is added to the reaction mixture and the insoluble product is filtered off and washed with methylene chloride (100 cc.). Water (100 cc.) is added to the organic filtrate and the product which separates out is filtered off and washed with methylene chloride (200 cc.). After drying, 6-(7-chloro-1,8-naphthyridin-2-yl)-5,7-dioxo-2,3,6,7-tetrahydro-5H-1,4-oxathiino[2,3-c]pyrrole (4.4 g.), melting at 264° C., is obtained.

2-Amino-7-chloro-1,8-naphthyridine can be prepared in accordance with the method described by S. Carboni et al., Gazz. Chem. Ital. 96, 1456 (1966).

EXAMPLE 6

Following the procedure of Example 4 but starting with 5-hydroxy-6-(5-nitropyrid-2-yl)-7-oxo-2,3,6,7-tetrahydro-5H-1,4-oxathiino[2,3-c]pyrrole (3.54 g.) and 1-chlorocarbonyl-4-methylpiperazine hydrochloride (7.2 g.) in methylene chloride (60 cc.) in the presence of triethylamine (6.75 cc.) and anhydrous pyridine (30 cc.), 5-(4-methylpiperazin-1-yl)carbonyloxy-6-(5-nitropyrid-2-yl)-7-oxo-2,3,6,7-tetrahydro-5H-1,4-oxathiino[2,3-c]pyrrole (3 g.), melting at 230° C., is obtained.

5-Hydroxy-6-(5-nitropyrid-2-yl)-7-oxo-2,3,6,7-tetrahydro-5H-1,4-oxathiino[2,3-c]pyrrole employed as starting material can be prepared by reaction of potassium borohydride (1.08 g.) with 6-(5-nitropyrid-2-yl)-5,7-dioxo-2,3,6,7-tetrahydro-5H-1,4-oxathiino[2,3-c]pyrrole (5.86 g.) in methanol (80 cc.) at a temperature of about 30° C. This gives 5-hydroxy-6-(5-nitropyrid-2-yl)-7-oxo-2,3,6,7-tetrahydro-5H-1,4-oxathiino[2,3-c]pyrrole (4.8 g.) melting at 272° C.

6-(5-Nitropyrid-2-yl)-5,7-dioxo-2,3,6,7-tetrahydro-5H-1,4-oxathiino[2,3-c]pyrrole can be prepared by reaction of 2-amino-5-nitropyridine (2.78 g.) with 5,6-dihydro-1,4-oxathiine-2,3-dicarboxylic acid anhydride (3.44 g.) in diphenyl ether (15 cc.) at a temperature of about 200° C. This gives 6-(5-nitropyrid-2-yl)-5,7-dioxo-2,3,6,7-tetrahydro-5H-1,4-oxathiino[2,3-c]pyrrole (3.9 g.) melting at 226° C.

2-Amino-5-nitropyridine can be prepared by the method described by D. J. Collins, J. Chem. Soc. (1963), 1337.

EXAMPLE 7

Following the procedure of Example 4 but starting with 5-hydroxy-6-(3-nitrophenyl)-7-oxo-2,3,6,7-tetrahydro-5H-1,4-oxathiino[2,3-c]pyrrole (3.53 g.) and 1-chlorocarbonyl-4-methylpiperazine hydrochloride (7.2 g.) in methylene chloride (60 cc.) in the presence of triethylamine (6.75 cc.) and anhydrous pyridine (30 cc.), 5-(4-methylpiperazin-1-yl)carbonyloxy-6-(3-nitrophenyl)-7-oxo-2,3,6,7-tetrahydro-5H-1,4-oxathiino[2,3-c]pyrrole (2.9 g.), melting at 170° C., is obtained.

5-Hydroxy-6-(3-nitrophenyl)-7-oxo-2,3,6,7-tetrahydro-5H-1,4-oxathiino[2,3-c]pyrrole employed as starting material can be prepared by reaction of potassium borohydride (1.19 g.) with 6-(3-nitrophenyl)-5,7-dioxo-2,3,6,7-tetrahydro-5H-1,4-oxathiino[2,3-c]-pyrrole (6.42 g.) in methanol (88 cc.) at a temperature of about 30° C. This gives 5-hydroxy-6-(3-nitrophenyl)-7-oxo-2,3,6,7-tetrahydro-5H-1,4-oxathiino[2,3-c]pyrrole (6 g.) melting at 110° C. and then at 222° C.

6-(3-Nitrophenyl)-5,7-dioxo-2,3,6,7-tetrahydro-5H-1,4-oxathiino[2,3-c]pyrrole can be prepared by reaction of 3-nitroaniline (2.76 g.) with 5,6-dihydro-1,4-oxathiine-2,3-dicarboxylic acid anhydride (3.44 g.) in diphenyl ether (15 cc.) at a temperature of about 200° C. This gives 6-(3-nitrophenyl)-5,7-dioxo-2,3,6,7-tetrahydro-5H-1,4-oxathiino[2,3-c]pyrrole (3.7 g.) melting at 166° C.

EXAMPLE 8

Following the procedure of Example 4 but starting with 5-hydroxy-6-(1,8-naphthyridin-2-yl)-7-oxo-2,3,6,7-tetrahydro-5H-1,4-oxathiino[2,3-c]pyrrole (5 g.) and 1-chlorocarbonyl-4-methylpiperazine hydrochloride (13.2 g.) in methylene chloride (69 cc.) in the presence of triethylamine (13.7 cc.) and anhydrous pyridine (50 cc.), 5-(4-methylpiperazin-1-yl)carbonyloxy-6-(1,8-naphthyridin-2-yl)-7-oxo-2,3,6,7-tetrahydro-5H-1,4-oxathiino[2,3-c]-pyrrole (3.28 g.), melting at 263° C. with decomposition, is obtained.

5-Hydroxy-6-(1,8-naphthyridin-2-yl)-7-oxo-2,3,6,7-tetrahydro-5H-1,4-oxathiino[2,3-c]pyrrole employed as starting material can be prepared by reaction of potassium borohydride (0.79 g.) with 6-(1,8-naphthyridin-2-yl)-5,7-dioxo-2,3,6,7-tetrahydro-5H-1,4-oxathiino[2,3-c]pyrrole (4.49 g.) in methanol (50 cc.) at a temperature of about 30° C. This gives 5-hydroxy-6-(1,8-naphthyridin-2-yl)-7-oxo-2,3,6,7-tetrahydro-5H-1,4-oxathiino[2,3-c]pyrrole (3 g.) melting at 162° C.

6-(1,8-Naphthyridin-2-yl)-5,7-dioxo-2,3,6,7-tetrahydro-5H-1,4-oxathiino[2,3-c]pyrrole can be prepared by heating a solution of 5,6-dihydro-1,4-oxathiine-2,3-dicarboxylic acid anhydride (6.88 g.) with N-hydroxysuccinimide (5.72 g.) in anhydrous dimethylformamide (200 cc.) at a temperature of about 60° C. After heating for 20 hours, 2-amino-1,8-naphthyridine (5.8 g.) and dicyclohexylcarbodiimide (24.72 g.) are added to the reaction mixture. The reaction mixture is then heated at a temperature of about 75° C. for 27 hours. After cooling, an insoluble material is filtered off and washed with methylene chloride (4 × 50 cc). Diisopropyl ether (700 cc.) is then added to the organic filtrate and the product which precipitates is filtered off and washed with diisopropyl ether (2 × 150 cc.). After drying, 6-(1,8-naphthyridin-2-yl)-5,7-dioxo-2,3,6,7-tetrahydro-5H-1,4-oxathiino[2,3-c]pyrrole (11 g.), melting at 200° C. and then at 227° C., is obtained.

2-Amino-1,8-naphthyridine can be prepared by the method described by W. W. Paudler and T.J. Kress, J. Org. Chem., 33. 1384 (1968).

EXAMPLE 9

Following the procedure of Example 4 but starting with 5-hydroxy-6-(6-methoxypyridazin-3-yl)-7-oxo- 2,3,6,7-tetrahydro-5H-1,4-oxathiino[2,3c]pyrrole (2.44 g.) and 1-chlorocarbonyl-4-methylpiperazine hydrochloride (6.05 g.) in methylene chloride (50 cc.) in the presence of triethylamine (7.1 cc.) and anhydrous pyridine (24.5 cc.), 5-(4-methylpiperazin-1-yl)carbonyloxy-6-(6-methoxypyridazin-3-yl)-7-oxo-2,3,6,7-tetrahydro-5H-1,4-oxathiino[2,3-c]pyrrole (2.32 g.), melting at 194° C., is obtained.

5-Hydroxy-6-(6-methoxypyridazin-3-yl)-7-oxo-2,3,6,7-tetrahydro-5H-1,4-oxathiino[2,3-c]pyrrole employed as starting material can be prepared by reaction of potassium borohydride (1.05 g.) with 6-(6-methoxypyridazin-3-yl)-5,7-dioxo-2,3,6,7-tetrahydro-5H-1,4-oxathiino[2,3-c]-pyrrole (6.2 g.) in methanol (63 cc.) at a temperature of about 25° C. 5-hydroxy-6-(6-methoxypyridazin-3-yl)-7-oxo-2,3,6,7-tetrahydro-5H-1,4-oxathiino[2,3-c]pyrrole (2.44 g.), melting at 165° C., is thus obtained.

6-(6-Methoxypyridazin-3-yl)-5,7-dioxo-2,3,6,7-tetrahydro-5H-1,4-oxathiino[2,3-c]pyrrole can be prepared by heating a solution of 5,6-dihydro-1,4-oxathiine-2,3-dicarboxylic acid anhydride (3.44 g.) with n-hydroxy-succinimide (2.86 g.) in anhydrous dimethylformamide (100 cc.) at a temperature of about 60° C. After heating for 19 hours, 3-amino-6-methoxypyridazine (3.52 g.) and dicyclohexylcarbodiimide (12.36 g.) are added to the reaction mixture. The reaction mixture is then heated at a temperature of about 75° C. for 8 hours. After cooling, an insoluble material is filtered off and washed with methylene chloride (3 × 25 cc.). Methylene chloride (300 cc.) is then added to the organic filtrate. The resulting solution is washed by decanting with water (4 × 200 cc.), and the organic phase is then dried over magnesium sulphate and evaporated to dryness. The residue obtained is taken up in diisopropyl ether (300 cc.) and the insoluble material is filtered off. After drying, 6-(6-methoxypyridazin-3-yl)-5,7-dioxo-2,3,6,7-tetrahydro-5H-1,4-oxathiino[2,3-c]pyrrole (6.3 g.), melting at 157° C., is obtained.

3-Amino-6-methoxypyridazine can be prepared by the method described by J. H. Clark et al., J. Amer. Chem. Soc., 80, 980 (1958).

EXAMPLE 10

Following the procedure of Example 4 but starting with 5-hydroxy-6-(7-methyl-1,8-naphthyridin-2-yl)-7-oxo-2,3,6,7-tetrahydro-5H-1,4-oxathiino[2,3-c]pyrrole (3.5 g.) abd 1-chlorocarbonyl-4-methylpiperazine hydrochloride (8.15 g.) in methylene chloride (70 cc.) in the presence of triethylamine (9.5 cc.) and anhydrous pyridine (35 cc.), 5-(4-methylpiperazin-1-yl)carbonyloxy-6-(7-methyl-1,8-naphthyridin-2-yl)-7-oxo-2,3,6,7-tetrahydro-5H-1,4-oxathiino[2,3-c]pyrrole(1.30 g.), melting at 258° C., is obtained.

5-Hydroxy-6-(7-methyl-1,8-naphthyridin-2-yl)-7-oxo-2,3,6,7-tetrahydro-5H-1,4-oxathiino[2,3-c]pyrrole employed as starting material can be prepared by reaction of potassium borohydride (0.69 g.) with 6-(7-methyl-1,8-naphthyridin-2-yl)-5,7-dioxo-2,3,6,7-tetrahydro-5H-1,4-oxathiino[2,3-c]pyrrole (4.7 g.) in methanol (50 cc.) at a temperature of about 25° C. This gives 5-hydroxy-6-(7-methyl-1,8-naphthyridin-2-yl)-7-oxo-2,3,6,7-tetrahydro-5H-1,4-oxathiino[2,3-c]pyrrole (3.6 g.) melting at 260° C.

6-(7-Methyl-1,8-naphthyridin-2-yl)-5,7-dioxo-2,3,6,7-tetrahydro-5H-1,4-oxathiino[2,3-c]pyrrole can be prepared by following the procedure of Example 9 but starting with a solution of 5,6-dihydro-1,4-oxathiine-2,3-dicarboxylic acid anhydride (3.44 g.) and N-hydroxysuccinimide (2.86 g.) in anhydrous dimethylformamide (100 cc.), to which 2-amino-7-methyl-1,8-naphthyridine (3.18 g.) and dicyclohexylcarbodiimide (8.24 g.) are added. This gives 6(7-methyl-1,8-naphthyridin-2-yl)-5,7-dioxo-2,3,6,7-tetrahydro-5H-1,4-oxathiino[2,3-c]-pyrrole (4.2 g.) melting at 233° C with decomposition.

2-Amino-7-methyl-1,8-naphthyridine can be prepared by the method described by E. V. Brown, J. Org. Chem., 30, 1607 (1965).

EXAMPLE 11

1-Allylpiperazine (6.3 g.) is added to a suspension of 6-(7-chloro-1,8-naphthyridin-2-yl)-7-oxo-5-phenoxycarbonyloxy-2,3,6,7-tetrahydro-5H-1,4-oxathiino[2,3-c]pyrrole(4.56 g.) in acetonitrile (25 cc.). The temperature of the reaction mixture rises to about 25° C. After 29 hours, diisopropyl ether (50 cc.) is added and the insoluble product is filtered off and washed with diisopropyl ether (2 × 15 cc.). After drying, 5-(4-allylpiperazine-1-yl)carbonyloxy-6-(7-chloro-1,8-naphthyridin-2-yl)-7-oxo-2,3,6,7-tetrahydro-5H-1,4-oxathiino[2,3-c]pyrrole(3.1 g.), melting at 254° C., is obtained.

6-(7-Chloro-1,8-naphthyridin-2-yl)-7-oxo-5-phenoxycarbonyloxy-2,3,6,7-tetrahydro-5H-1,4-oxathiino[2,3-c]pyrrole employed as starting material can be prepared by adding phenyl chloroformate (9.4 g.) to a solution of 6-(7-chloro-1,8-naphthyridin-2-yl)-5-hydroxy-7-oxo-2,3,6,7-tetrahydro-5H-1,4-oxathiino[2,3-c]pyrrole (6.71 g.) in pyridine (70 cc.). The reaction mixture is then heated to a temperature of about 50° C. for 1 hour 15 minutes. After cooling to a temperature of about 10° C., water (400 cc.) is added. The insoluble product is filtered off and washed with water (2 × 50 cc.), acetonitrile (2 × 30 cc.) and diisopropyl ether (50 cc.). After drying, 6-(7-chloro-1,8-naphthyridin-2-yl)-7-oxo-5-phenoxycarbonyloxy-2,3,6,7-tetrahydro-5H-1,4-oxathiino[2,3-c]pyrrole (7.3 g.) melting at 270° C. is obtained.

1-Allylpiperazine can be prepared in accordance with the method described by Ikeda Yoshiaki et al., Yakugaku Zasshi, 89(5), 669 (1969).

The present invention includes within its scope pharmaceutical compositions comprising, as active ingredient, at least one of the compounds of general formula I, or a non-toxic acid addition salt thereof, in association with a pharmaceutical carrier or coating. The invention includes especially such preparations made up for oral, parenteral or rectal administration or as ointments.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy because of their tranqullising effect, their anti-convulsant effect, their effect in overcoming contractures and their effect in producing hypnosis. In human therapy the compositions when administered orally to an adult should generally give doses between 10 mg. and 500 mg. of active substance per day. In general the physician will decide the posology considered appropriate, taking into account the age and weight and other factors intrinsic to the patient being treated.

The following Example illustrates pharmaceutical compositions according to the invention.

EXAMPLE 12

Tablets containing 25 mg. of active product and having the following composition are prepared in accordance with the usual technique:
6-(5-chloropyrid-2-yl)-5-(4-methylpiperazin-1-yl)carbonyloxy-7-oxo-2,3,6,7-tetrahydro-5H-1,4-oxathiino[2,3-c]pyrrole — 0.025 g.
starch — 0.090 g.
precipitated silica — 0.030 g.
magnesium stearate — 0.005 g.

We claim:
1. A 1,4-oxathiino[2,3-c]pyrrole derivative of the formula:

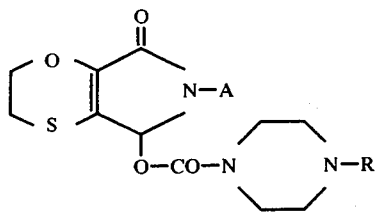

wherein A represents a phenyl, 2-pyridyl, 2-quinolyl or 1,8-naphthyridinyl radical, or a said radical substituted by a halogen atom or a methyl, methoxy or nitro radical, and R represents methyl or alkenyl of 2 through 4 carbon atoms.

2. A 1,4-oxathiino[2,3-c]pyrrole derivative according to claim 1 wherein A represents a 2-pyridyl, 2-quinolyl or 1,8-naphthyridin-2-yl radical substituted by a chlorine atom or a methyl or methoxy radical, and R represents methyl or allyl.

3. The 1,4-oxathiino[2,3-c]pyrrole derivative according to claim 1 which is 6-(7-methoxy-1,8-naphthyridin-2-yl)-5-(4-methylpiperazin-1-yl)-carbonyloxy-7-oxo-2,3,6,7-tetrahydro-5H-1,4-oxathiino[2,3-c]pyrrole or a non-toxic pharmaceutically acceptable acid addition salt thereof.

4. The 1,4-oxathiino[2,3-c]pyrrole derivative according to claim 1 which is 6-(7-chloroquinol-2-yl)-5-(4-methylpiperazin-1-yl)carbonyloxy-7-oxo-2,3,6,7-tetrahydro5H-1,4-oxathiino[2,3-c]pyrrole or a non-toxic pharmaceutically acceptable acid addition salt thereof.

5. The 1,4-oxathiino[2,3-c]pyrrole derivative according to claim 1 which is 6-(5-chloropyrid-2-yl)-5-(4-methylpiperazine-1-yl)carbonyloxy-7-oxo-2,3,6,7-tetrahydro5H-1,4-oxothiino[2,3-c]pyrrole or a non-toxic pharmaceutically acceptable acid addition salt thereof.

6. The 1,4-oxathiino[2,3-c]pyrrole derivative according to claim 1 which is 5-(4-methylpiperazin1-yl)-carbonyloxy-6-(5-methylpyrid-2-yl)-7-oxo-2,3,6,7-tetrahydro-5H-1,4-oxathiino[2,3-c]pyrrole or a non-toxic pharmaceutically acceptable acid addition salt thereof.

7. The 1,4-oxathiino[2,3-c]pyrrole derivative according to claim 1 which is 6-(7-chloro-1,8-naphthyridin-2-yl)-5-(4-methylpiperazine-1-yl)carbonyloxy-7-oxo-2,3,6,7-tetrahydro-5H-1,4-oxathiino[2,3-c]pyrrole or a non-toxic pharmaceutically acceptable acid addition salt thereof.

8. The 1,4-oxathiino[2,3-c]pyrrole derivative according to claim 1 which is 5(4-allylpiperazin-1-yl)-carbonyloxy-6-(7-chloro-1,8naphthyridin-2yl)-7-oxo-2,3,6,7-tetrahydro-5H-1,4-oxathiino[2,3-c]pyrrole or a non-toxic pharmaceutically acceptable acid addition salt thereof.

9. A pharmaceutical composition consisting essentially of as active ingredient, an effective amount of a 1,4-oxathiino [2,3-c]pyrrole as defined in claim 1, or a non-toxic pharmaceutically acceptable acid addition salt thereof, in association with a significant amount of a pharmaceutical carrier.

* * * * *